(12) United States Patent
Cormier et al.

(10) Patent No.: US 6,219,574 B1
(45) Date of Patent: *Apr. 17, 2001

(54) DEVICE AND METHOD FOR ENCHANCING TRANSDERMAL SAMPLING

(75) Inventors: Michel J. N. Cormier, Mountain View; Felix T. Theeuwes, Los Altos Hills, both of CA (US)

(73) Assignee: Alza Corporation, Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/876,989

(22) Filed: Jun. 17, 1997

Related U.S. Application Data

(60) Provisional application No. 60/019,990, filed on Jun. 18, 1996.

(51) Int. Cl.$^7$ ................................................ A61N 1/30
(52) U.S. Cl. ........................... 604/20; 600/578; 600/583; 600/362
(58) Field of Search .................. 604/20–21; 600/573, 600/583, 578, 362

(56) References Cited

U.S. PATENT DOCUMENTS

| | | | |
|---|---|---|---|
| 2,893,392 | 7/1959 | Wagner et al. | 128/253 |
| 3,072,122 | 1/1963 | Rosenthal | 128/253 |
| 3,623,475 * | 11/1971 | Sanz . | |
| 3,814,097 * | 6/1974 | Ganderton et al. . | |
| 3,845,770 | 11/1974 | Theeuwes et al. | 128/260 |
| 3,916,899 | 11/1975 | Theeuwes et al. . | |
| 3,964,482 * | 6/1976 | Gerstel et al. . | |
| 4,014,334 | 3/1977 | Theeuwes et al. | 128/260 |
| 4,077,407 | 3/1978 | Theeuwes et al. | 128/260 |
| 4,340,048 | 7/1982 | Eckenhoff | 128/213 R |
| 4,655,766 | 4/1987 | Theeuwes et al. | 604/896 |
| 4,753,651 | 6/1988 | Eckenhoff | 424/449 |
| 4,756,314 | 7/1988 | Eckenhoff et al. | 128/760 |
| 5,036,861 | 8/1991 | Sembrowich et al. | 128/763 |
| 5,139,023 * | 8/1992 | Stanley et al. . | |
| 5,158,537 * | 10/1992 | Haak et al. . | |
| 5,250,023 | 10/1993 | Lee et al. | 604/20 |
| 5,279,543 * | 1/1994 | Glikfeld et al. . | |
| 5,279,544 * | 1/1994 | Gross et al. . | |
| 5,291,887 * | 3/1994 | Stanley et al. . | |
| 5,362,307 | 11/1994 | Guy et al. | 604/20 |
| 5,438,984 | 8/1995 | Schoendorfer | 128/632 |
| 5,582,184 * | 12/1996 | Erickson et al. . | |
| 5,582,586 * | 12/1996 | Tachibana et al. . | |

FOREIGN PATENT DOCUMENTS

| | | | |
|---|---|---|---|
| 1296174 * | 3/1987 | (SU) . | |
| WO 92/10234 | 6/1992 | (WO) | A61N/1/30 |
| WO 94/05368 | 3/1994 | (WO) | A61N/1/30 |
| WO 96/00110 | 1/1996 | (WO) | A61N/1/30 |
| WO 96/17648 | 6/1996 | (WO) | A61N/1/30 |
| WO 97/07734 | 3/1997 | (WO) | A61B/5/00 |

OTHER PUBLICATIONS

Reiss, Susan M., Biophotonic International, May/Jun. 1997, pp 43–45, Glucose–and Blood–Monitoring.

Eppstein, Jonathan, M.S., et al. "Rapid Transdermal Drug Delivery With Thermal Micro–Poration" presented at a Transdermal Delivery Conference in San Diego on Dec./ 15–18, 1997 sponsored by IBC.

\* cited by examiner

*Primary Examiner*—Mark Bockelman
(74) *Attorney, Agent, or Firm*—Owen J. Bates; D. Byron Miller; Steven F. Stone

(57) ABSTRACT

A percutaneous agent sampling device and method are provided. The device comprises a collector and a sheet having a plurality of microblades for piercing the skin for increasing transdermal flux of an agent.

28 Claims, 3 Drawing Sheets

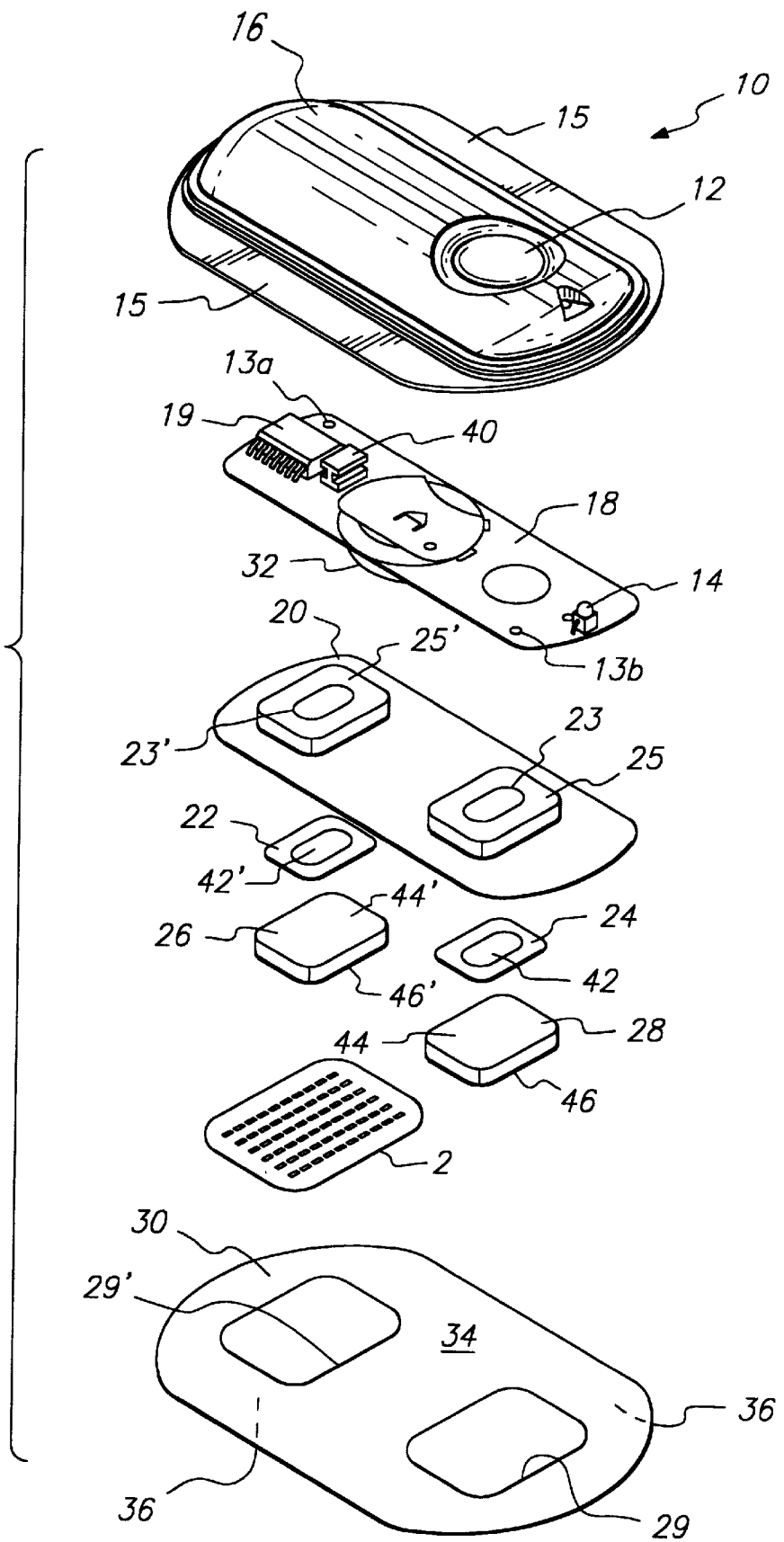

DEVICE AND METHOD FOR ENCHANCING TRANSDERMAL SAMPLING

CROSS-REFERENCE TO RELATED APPLICATIONS

A claim is made, under 35 USC § 119(e), to the benefit of the filing of U.S. patent application Ser. No. 60/019,990 filed Jun. 18, 1996.

TECHNICAL FIELD

The present invention relates to transdermal agent sampling. More particularly, this invention relates to the transdermal sampling of agents, such as glucose, electrolyte and substances of abuse, such as but not limited to alcohol and illicit drugs. The present invention uses skin-piercing microblades to enhance the transdermal flux of the agents during transdermal sampling.

BACKGROUND ART

Interest in the percutaneous or transdermal sampling of agents continues to grow. The transdermal sampling of agents still faces significant problems. In many instances, the flux of agents through the skin is insufficient to calculate quickly and accurately the concentration of the sampled substance in the blood or body.

One method of increasing the transdermal sampling of agents relies on the application of an electric current across the body surface or on "electrotransport". "Electrotransport" refers generally to the passage of an agent through a body surface such as skin, mucous membranes, nails, and the like. The transport of the agent is induced or enhanced by the application of an electrical potential, which results in the application of electric current, which samples or enhances sampling of the agent. The electrotransport of agents through a body surface may be attained in various manners. One widely used electrotransport process, iontophoresis, involves the electrically induced transport of charged ions. Electroosmosis, another type of electrotransport process, involves the movement of a solvent with the agent through a membrane under the influence of an electric field. Electroporation, still another type of electrotransport, involves the passage of an agent through pores formed by applying a high voltage electrical pulse to a membrane. In many instances, more than one of these processes may be occurring simultaneously to different extents. Further increases in transdermal sampling rates are highly desirable.

One method of increasing the agent transdermal sampling rate involves pre-treating the skin with a skin permeation enhancer. The term "permeation enhancer" is broadly used herein to describe a substance which, when applied to a body surface through which the agent is sampled, enhances its transdermal flux. The mechanism may involve an increase in the permeability of the body surface, or in the case of electrotransport sampling, a reduction of the electrical resistance of the body surface to the passage of the agent therethrough and/or the creation of hydrophilic pathways through the body surface during electrotransport.

There have been many attempts to enhance transdermal flux by mechanically puncturing the skin prior to transdermal drug delivery. See for example U.S. Pat. No. 5,279,544 issued to Gross et al., U.S. Pat. No. 5,250,023 issued to Lee et al., and U.S. Pat. No. 3,964,482 issued to Gerstel et al. These devices utilize tubular or cylindrical structures generally, although Gerstel does disclose the use of other shapes, to pierce the outer layer of the skin for agent delivery, but not sampling. Each of these devices provide manufacturing challenges, limited mechanical attachment of the structure to the skin, and/or undesirable irritation of the skin.

As has been discussed, a variety of chemicals and mechanical means have been explored to enhance transdermal flux. However, there is still a need to provide a device suitable for increasing transdermal flux which device is low-cost and which can be manufactured reproducibly (i.e., without significant variation from device to device) in high volume production.

DESCRIPTION OF THE INVENTION

The present invention provides a reproducible, high volume production, low-cost device suitable for increasing transdermal flux for agent sampling and monitoring. The invention comprises a plurality of microblades for piercing the skin. The microblades typically have a length of less than about 0.5 mm and a width and thickness which is even smaller. In spite of their small size, the microblades can be made with an extremely reproducible size and shape so that the microslits formed by the microblades puncturing the skin also have a very reproducible size and depth. Because the microblades have a small thickness (i.e., small relative to the width and length of the blades), the microblades produce less tissue damage for a given cross-section than a skin piercing microneedle having a circular cross-section. The device of the present invention pierces the stratum corneum of a body surface to form pathways through which an agent (e.g., a body electrolyte) can be withdrawn (i.e., sampled or monitored).

In one aspect of the invention, the device comprises a sheet having a plurality of microblades integral therewith and extending downward therefrom and a collector on the sheet which collects an agent which is withdrawn through the pathways in the skin formed by the microblades. The device of the present invention can be used in connection with body analyte or drug sampling, or both. Collectors (i.e., sampling devices) for use with the present invention include, but are not limited to, "reverse" electrotransport devices as disclosed in Glikfeld et al., U.S. Pat. No. 5,279,543 and Guy et al., U.S. Pat. No. 5,362,307, passive diffusion devices as disclosed in Schoendorfer for U.S. Pat. No. 5,438,984, osmotic devices as disclosed in Eckenhoff et al., U.S. Pat. No. 4,756,314 and negative pressure driven devices.

BRIEF DESCRIPTION OF THE DRAWINGS

FIG. 6 is a perspective exploded view of one embodiment of a "reverse" electrotransport agent sampling system with a microblade array device according to one embodiment of the present invention;

MODES FOR CARRYING OUT THE INVENTIONS

Figure 1:
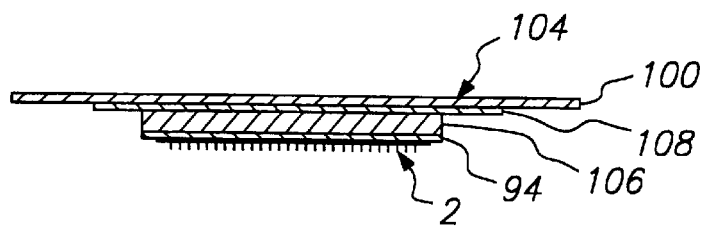
FIG. 1 is a diagrammatic cross-sectional view of a sampling system in accordance with one embodiment of the present invention.

Turning now to the drawings in detail, one embodiment of a sampling device of the present invention is generally shown in FIG. 1. FIG. 1 illustrates an osmotic collector or sampling device 104 in combination with a skin-piercing microblade array member 2. The osmotic collector 104 is attached to a body surface by means of an impermeable flexible adhesive overlay 100. Collector 104 is comprised of an absorbent pad (which is impregnated with an osmotically active material such as a highly soluble salt) 106 located between a semi-permeable or osmotic membrane 94 and an optional agent sensing element 108. The semi-permeable member 94 is permeable to water and the agent to be collected and impermeable to the osmotically active material. Any of a wide variety of natural and synthetic semi-permeable membranes are known in the art as osmotic membranes. Suitable membranes are enumerated in U.S. Pat. Nos. 3,845,770, 3,916,899, 4,077,407 and 4,014, 334, all of which are incorporated herein by reference.

The pad 106 preferably has dispersed therethrough sufficient undissolved osmotic agent such that the concentration of the solution formed within the collection pad as a result of the imbibition of water through the semi-permeable membrane 94 will be maintained at the saturation level throughout the intended sampling period. The pad 106 may also contain dispersed therethrough a collecting material such as colloidal silica, ion exchange resins, activated charcoal or other materials that selectively adhere to the agent being collected to prevent back diffusion of the agent through the membrane 94.

The optional agent sensing element can be any of a variety of chemically reactive sensors and indicators, for example the color indicating test strips associated with glucose testing. The adhesive overlay 100 can have a cut-out or transparent window in the area of the indicators so that the indicators can be readily viewed. In an alternate embodiment, the agent sensing element can be located between the member 2 and the pad 106. Alternatively, pad 106 and osmotic membrane 94 are combined in one layer of absorbent hydrogel that stores the absorbed fluid as well as the agent. Preferably, the pad 106 is free to expand or is encapsulated in the semi-permeable or osmotic membrane 94 so that it retains the fluid therein.

Member 2 is used in conjunction with the percutaneous sampling of an agent. The term "sampling" is used broadly herein to include withdrawal of or monitoring the presence or amount of an agent. The terms "substance" and "agent" are used interchangeably herein and broadly include substances such as glucose, body electrolytes, alcohol, illicit drugs, licit substances, pharmaceuticals, blood gases, etc. that can be sampled through the skin. The major barrier properties of the skin, such as resistance to agent passage, reside with the outer most layer (i.e., stratum corneum). The inner division of the epidermis generally comprises three layers commonly identified as stratum granulosum, stratum Malpighi, and stratum germinativum. There is essentially little or no resistance to movement of an agent through the stratum granulosum, stratum Malpighi, and stratum germinativum. The device of the present invention is used to form microslits in the stratum corneum for in situ sampling of an agent.

Figure 2:
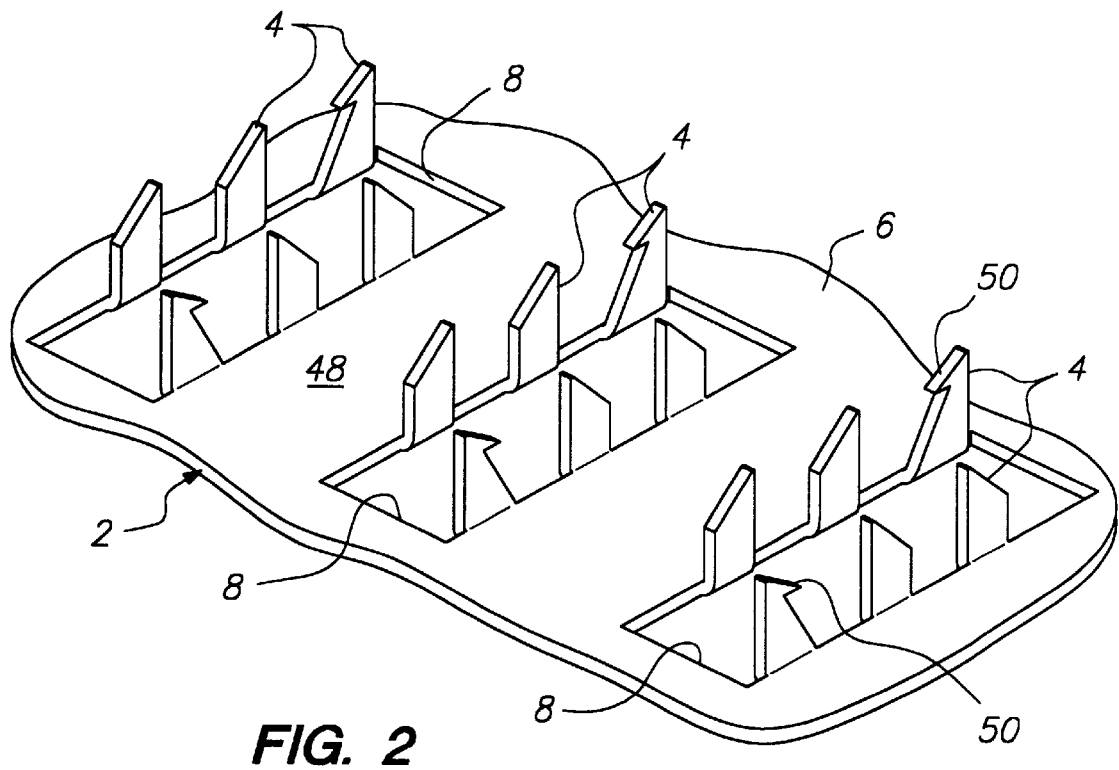
FIG. 2 is an enlarged perspective view of the skin proximal side of the mircroblade array device which may be used in the present invention.

Member 2 comprises a plurality of microblades 4 (i.e., a blade array) extending downward from one surface of a sheet 6 (see FIG. 2 in which a portion of member 2 is in an inverted position to show the microblades). The microblades 4 are sized and shaped to penetrate the stratum corneum of the epidermis when pressure is applied to the device but do not penetrate the 8 skin sufficiently to contact the patient's nerve endings. With this configuration, the microblades do not cause a painful sensation or bleeding. The microblades 4 form microslits in a body surface to increase the sampling of a substance through the body surface. The term "body surface" as used herein refers generally to the skin of an animal or human. Placement of the member 2 in conjunction with a sampling system associated therewith on the body surface of a patient allows in situ sampling and monitoring without relying on collecting a blood sample with a needle and syringe or lance and test strip. In one preferred embodiment, the device is designed to monitor glucose levels in diabetic patients. In the case of agent (e.g., body analyte) sampling, the analyte migrates from the body through the microslits in the stratum corneum which are cut by the microblades 4. The sampled agent may be collected directly from the skin, or the agent may be contained in the interstitial fluid and/or sweat of the patient and the latter fluid can be collected for purposes of sampling the agent.

Figure 3:
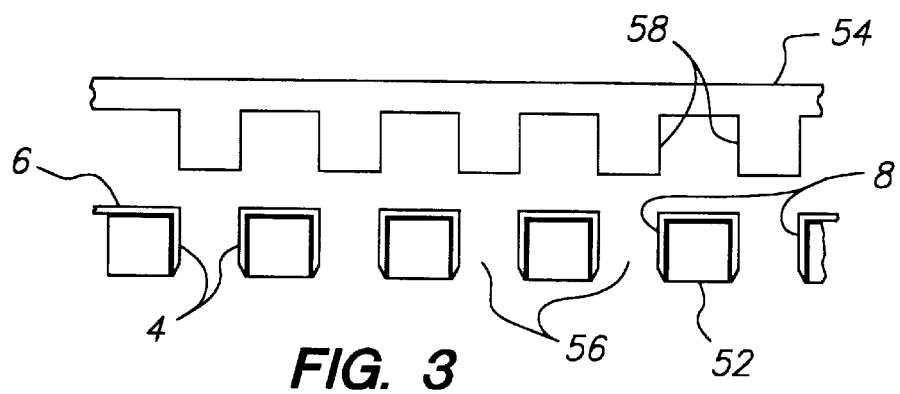
FIG. 3 is a diagrammatic representation of a method for producing a microblade array used in the present invention.

In one embodiment, the opening 8 corresponds to the portion of the sheet 6 occupied by each of the microblades prior to the blades being transpositioned into the downward depending position. In the illustrated embodiment (FIGS. 2 and 3), the sheet 6 is formed with an opening 8 between the microblades 4. The opening 8 corresponds to the portion of the sheet 6 occupied by each of the microblades 4 prior to the microblades being bent into a position which is substantially perpendicular to the plane of sheet 6. The number of openings 8 per device and the number of microblades 4 per device are independent. The device may have only one large opening 8 with a plurality of microblades 4 around the opening. As will be described below, the opening 8 may be covered with an agent-attracting member for enhancing the movement of an agent being sampled into an agent-collecting reservoir.

The microblades 4 are generally formed from a single piece of material (although they need not be) and are sufficiently sharp and long for puncturing at least the stratum corneum of the body surface. In one embodiment, the microblades 4 and the sheet 6 are essentially impermeable or are impermeable to the passage of an agent. The width of each microblade can be any of a range of widths. Usually, the width of the microblade is in the range of about 25 μm to 500 μm. The length of the microblades is subject to variation of the body surface being penetrated and corresponds to the natural thickness of the stratum corneum. Usually, the microblades 4 will be about 20 μm to about 400 μm in length. The microblades 4 can have slanted (i.e., angled) leading edges 64 (FIG. 2) to further reduce the insertion force required to press the microblades 4 into the body surface. The leading edges 64 of each microblade can be all the same angle or can be at different angles suitable for piercing the body surface. The leading edge can have multiple segments with the distal most segment having a smaller angle with respect to an axis along the length of the microblade than a more proximal segment. Alternatively, the leading edge of each microblade can be arcuate (i.e., curved) in shape, having, for example, a convex or concave shape.

The member 2 can also improve the attachment of the device to the body surface so that continuous agent detection through the body surface is preserved during movement of the body surface. In the embodiment shown in FIG. 2, projections in the form of barbs 50 on at least one of the microblades 4 assist in anchoring the member 2 and any corresponding device or structure used in combination therewith to the body surface. Barbs 50 can be on any number of the microblades from one to all microblades. The barbs 50 are optional as other means for holding the member in contact with the body surface can be used. The present invention can be used in conjunction with a wide variety of microblades configurations, for example, reference may be had to U.S. Provisional Application Ser. No. 60/019,990 filed Jun. 18, 1996 of which any of the disclosed configurations can be used with the present invention.

The pattern for any of the microblade array members 2 of the present invention can be produced with a photo-etching process. For example, reference may be had to U.S. Provisional Application Ser. No. 60/019,990 filed Jun. 18, 1996 of which any of the disclosed methods can be used to produce the member 2 of the present invention. A thin sheet 6 of metal such as stainless steel or titanium is etched photolithographically with patterns containing skin piercing structures. In general, a thin laminate dry resist or wet resist is applied on the sheet 6 which typically has a thickness of about 7 $\mu$m to about 100 $\mu$m, preferably about 25 $\mu$m to about 50 $\mu$m. The resist is contact exposed using a mask having the desired pattern and is subsequently developed. These operations are conducted in much the same way that they are for the manufacture of a printed circuit board. The sheet 6 is then etched using acidic solutions. After the pattern has been etched through the sheet, the sheet 6 is placed on a die 52 (FIG. 3) having a plurality of openings 56 corresponding to the openings 8 in the sheet. A punch 54 having a plurality of protrusions 58 corresponding to the openings 8 in the sheet 6 and openings 56 in the die 52 is initially located above the sheet 6 and the die 52. At the initial stage, the microblades 4 are in the same plane as the rest of the sheet 6. The punch protrusions 58 are then pressed into the openings 8, thus bending the microblades downward to be substantially perpendicular to the plane of the sheet 6. The finished structure provides microblades 4 with an adjacent opening 8. In one embodiment, the opening 8 allows the passage of interstitial fluid therethrough when the member 2 is applied to the body surface. Rectangular openings 8 are shown in the figures but the invention encompasses the use of any shape openings including, but not limited to, square, triangular, circular and elliptical.

Generally, the microblades 4 are at an angle of about 90° to the surface 48 (FIG. 2) of the sheet 6 after being punched, but they can be disposed at any angle forward or backward from the perpendicular position that will facilitate penetration of and attachment to the body surface. In addition, other anchoring elements such as barbs, openings, etc. can be used with the angled microblades to further enhance anchoring of the device.

The member 2 can optionally be made to adhere to the patient's body surface by various means, including an adhesive applied to the body-contacting side of sheet 6 or other anchoring elements on the member 2 of any of the embodiments discussed herein. Further, a watch band or elastic bandage can be used to maintain the device in contact with the skin. The adhesive should have sufficient tack to insure that the member 2 remains in place on the body surface during normal user activity, and yet permits reasonable removal after the predetermined (e.g., 24-hour) wear period. A suitable release liner (not shown) is preferably provided for maintaining the integrity of the adhesive before use. In use, the release liner is stripped from the adhesive before the device is applied to the skin.

As is best shown in FIG. 2, the microblades 4 have a thickness which is much smaller than the width of the blades near their base, i.e., near the point where the blades are attached to the sheet 6. This blade geometry provides maximum agent percolation area with a minimum blade penetration area, and hence less tissue damage. The agent percolation area is the area of the microslit opening(s) formed in the stratum corneum by the blade(s), less the cross-sectional area of the blade(s). The microblades are shaped with the largest possible surface area with a minimal cross-sectional area so as to give the largest possible percolation area. Thin microblades are better than round protrusions for this purpose because for the same cross-section, a thin blade produces more percolation area and less tissue damage than a round protrusion. This is a crucial advantage over the prior art round elements such as needles and tubes. Thin microblades also require less insertion force than round protrusions. The width of each blade can be any of a range of widths. The widths can be different from blade to blade in the array pattern. Likewise, the width can be variable along the length of the blade, as will be described in more detail below. The width of the blade at the intersection of the blade and the body surface after the blade array has been inserted is preferably in the range of about 25 $\mu$m to about 500 $\mu$m, more preferably about 50 $\mu$m to about 400 $\mu$m, more preferably 100 $\mu$m to about 300 $\mu$m.

The sheet 6 and microblades 4 can be made from materials that have sufficient strength and manufacturability to produce blades, such as, glasses, ceramics, rigid polymers, metals and metal alloys. Examples of metals and metal alloys include but are not limited to stainless steel, iron, steel, tin, zinc, copper, platinum, aluminum, germanium, nickel, zirconium, titanium and titanium alloys consisting of nickel, molybdenum and chromium, metals plated with nickel, gold, rhodium, iridium, titanium, platinum, and the like. An example of glasses include a devitrified glass such as "PHOTOCERAM" available from Corning in Corning, NY. Examples of polymers include but are not limited to rigid polymers such as polystyrene, polymethylmethacrylate, polypropylene, polyethylene, "BAKELITE", cellulose acetate, ethyl cellulose, styrene/acrylonitrile copolymers, styrene/butadiene copolymers, acrylonitrile/butadiene/styrene (ABS) copolymers, polyvinyl chloride and acrylic acid polymers including polyacrylates and polymethacrylates.

The number of microblades 4 and openings 8 of any of the embodiments of the member 2 is variable with respect to the desired flux rate, agent being sampled, sampling device used (i.e., reverse electrotransport, passive diffusion, osmotic, suction, etc.), and other factors as will be evident to one of ordinary skill in the art. In general, the larger the number of blades per unit area (i.e., the blade density), the more distributed is the flux of the agent through the skin because there are a greater number of agent-conveying pathways through the skin. Consequently, the smaller the number of blades per unit area, the more concentrated is the flux of the agent through the skin because there are fewer pathways. The present invention has a blade density of at least about 10 blades/$cm^2$ and less than about 1000 blades/$cm^2$, preferably at least about 600 blades/$cm^2$, more preferably at least about 800 blades/cm$^2$. In similar fashion, the number of openings per unit area through which the agent passes is at least about 10 openings/cm$^2$ and less than about 1000 openings/cm$^2$. In one embodiment, the present invention produces a percolation area of about 0.005 to 0.05 cm$^2$/cm$^2$ of body surface, preferably about 0.01 cm$^2$/cm$^2$ of body surface.

Figure 4:
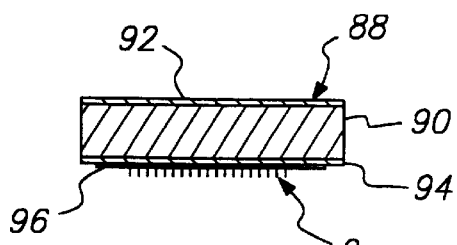
FIG. 4 is a diagrammatic cross-sectional view of a passive agent sampling system in accordance with one embodiment of the present invention.
Figure 5:
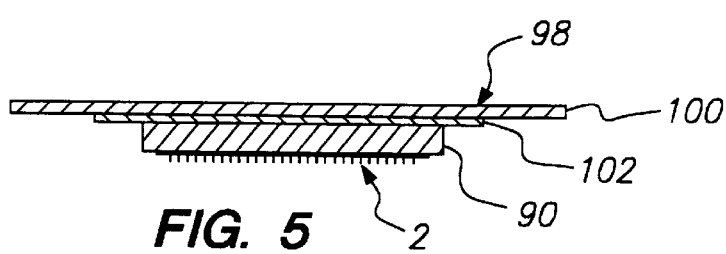
FIG. 5 is a diagrammatic cross-sectional view of another embodiment of a passive agent sampling system in accordance with the present invention.
Figure 7:
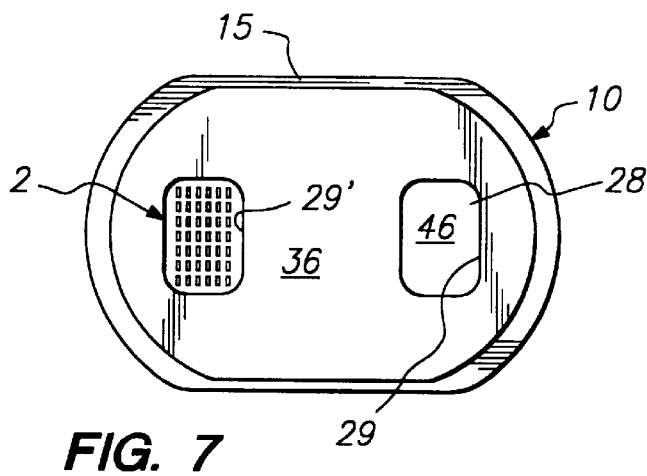
FIG. 7 is a bottom plan view of the "reverse" electrotransport agent sampling system of FIG. 6.
Figure 8:
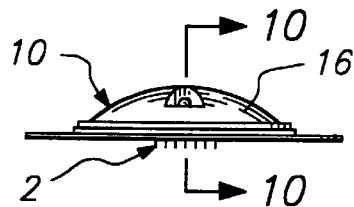
FIG. 8 is a right side elevational view of the "reverse" electrotransport agent sampling system of FIG. 6.
Figure 9:
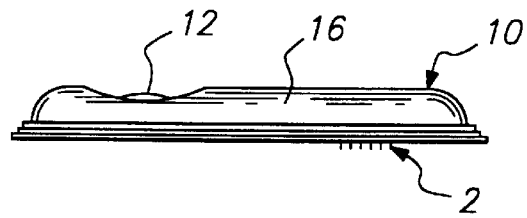
FIG. 9 is a rear elevational view of the "reverse" electrotransport agent sampling system of FIG. 6.
Figure 10:
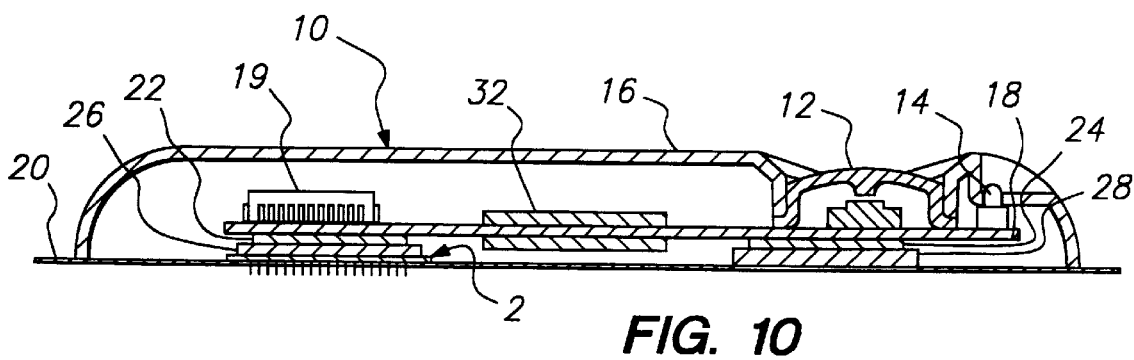
FIG. 10 is a cross-sectional view taken along line 10—10 of the assembled "reverse" electrotransport agent sampling system of FIG. 8.

In other embodiments of the present invention, passive transdermal sampling devices are used with member 2. Two examples of passive transdermal sampling devices are illustrated in FIGS. 4 and 5. In FIG. 4, passive transdermal sampling device 88 comprises a reservoir 90 sandwiched between a backing layer 92, which is preferably impermeable to the agent, and a wicking membrane 94. In FIG. 4, the reservoir 90 is formed of a material, such as a rubbery polymer, that is sufficiently viscous to maintain its shape. If a lower viscosity material is used for reservoir 90, such as an aqueous gel, backing layer 92 and wicking membrane 94 would be sealed together about their periphery to prevent leakage. Located below membrane 94 is microblade array member 2. The device 88 adheres to a body surface by means of contact adhesive layer 96 around the periphery of the member 2. A strippable release liner (not shown) is normally provided along the exposed surface of adhesive layer 96 and is removed prior to application of device 88 to the body surface.

Alternatively, as shown in FIG. 5, transdermal sampling device 98 may be attached to a body surface by means of a flexible adhesive overlay 100. Device 98 is comprised of an impermeable backing layer 102 adjacent one surface of reservoir 90. Adhesive overlay 100 maintains the device 98 on the body surface. Adhesive overlay 100 can be fabricated together with, or provided separately from, the remaining elements of the device 98. With certain formulations, the adhesive overlay 100 may be preferable to the contact adhesive 96 shown in FIG. 4. This is true, for example, where the agent reservoir contains a material (such as, for example, an oily surfactant permeation enhancer) which adversely affects the adhesive properties of the contact adhesive layer 96. Impermeable backing layer 102 is preferably slightly larger than reservoir 90, and in this manner prevents the agent collected in reservoir 90 from adversely interacting with the adhesive in overlay 100. A wicking membrane (not shown in FIG. 5) similar to membrane 94 in device 88 (FIG. 4) is located on the skin/mucosa side of reservoir 90. A strippable release liner (not shown) is also normally provided with device 98 and is removed just prior to application of device 98 to the body surface.

One embodiment of the present invention relies on the application of an electric current across the body surface or "electrotransport". Electrotransport refers generally to the passage of an agent through a body surface such as skin, mucous membranes, nails, and the like. The transport of the agent is induced or enhanced by the application of an electrical potential, which results in the application of electric current, which for "reverse" electrotransport, samples or enhances sampling of the agent. The electrotransport of the agents out of the skin may be attained in various manners. One widely used electrotransport process, iontophoresis, involves the electrically induced transport of charged ions. Electroosmosis, another type of electrotransport process involved in the transdermal transport of uncharged or neutrally charged molecules (e.g., transdermal sampling of glucose), involves the movement of a solvent with the agent through a membrane under the influence of an electric field. Electroporation, still another type of electrotransport, involves the passage of an agent through pores formed by applying an electrical pulse, a high voltage pulse, to the skin. In many instances, more than one of these processes may be occurring simultaneously to different extents. Accordingly, the term "electrotransport" is given herein its broadest possible interpretation, to include the electrically induced or enhanced transport of at least one charged or uncharged agent, or mixtures thereof, regardless of the specific mechanism(s) by which the agent is actually being transported.

It will be appreciated by those working in the field that the present invention can be used in conjunction with a wide variety of electrotransport systems, as the invention is not limited in any way in this regard. For examples of electrotransport drug sampling systems, reference may be had to U.S. Pat. No. 5,279,543 to Glikfeld et al. and U.S. Pat. No. 5,362,307 to Guy et al., the disclosures of which are incorporated by reference herein in their entirety.

Electrotransport devices generally use at least two electrodes which are in electrical contact with some portion of the skin, nails, mucous membrane, or other body surface. In the case of transdermal agent sampling, one of the two electrodes is referred to as the "receptor" electrode, and is the one into which the agent (e.g., body analyte) is collected after being withdrawn from the body. The second electrode is typically termed the "counter" or "return" electrode and serves to close the electrical circuit through the body. For example, when the agent to be sampled is a cation, the cathode becomes the receptor electrode while the anode serves to complete the circuit. When the agent to be sampled is an anion, the anode becomes the receptor electrode while the cathode serves to complete the circuit. When the agent to be sampled has no net charge (e.g., glucose), then either the anode or the cathode, or both electrodes can serve as the receptor electrode.

FIGS. 6–10 illustrate a representative reverse electrotransport sampling device 10 that may be used in conjunction with the present invention. Device 10 comprises an upper housing 16, a circuit board assembly 18, a lower housing 20, first electrode 22, second electrode 24, electrically conductive gel reservoir 26, electrically conductive gel reservoir 28 and skin-compatible adhesive 30. Upper housing 16 has lateral wings 15 which assist in holding device 10 on a patient's skin. Printed circuit board assembly 18 comprises an integrated circuit 19 coupled to discrete components 40 and battery 32. Circuit board assembly 18 is attached to housing 16 by posts (not shown in FIG. 1) passing through openings 13a and 13b, the ends of the posts being heated/melted in order to heat stake the circuit board assembly 18 to the housing 16. Lower housing 20 is attached to the upper housing 16 by means of adhesive layer 30, the upper surface 34 of adhesive layer 30 being adhered to both lower housing 20 and upper housing 16 including the bottom surfaces of wings 15. Shown (partially) on the underside of circuit board assembly 18 is a button cell battery 32. Other types of batteries may also be employed to power device 10 depending on the need.

The device 10 is generally comprised of battery 32, electronic circuitry 19,40, electrodes 22,24, conductive gel reservoirs 26,28, and device 2, all of which are integrated into a self-contained unit. The outputs (not shown in FIG. 1) of the circuit board assembly 18 make electrical contact with the electrodes 24 and 22 through openings 23,23' in the depressions 25,25' formed in lower housing 20, by means of electrically conductive adhesive strips 42,42'. Electrodes 22 and 24, in turn, are in direct mechanical and electrical contact with the top sides 44',44 of conductive gel reservoirs 26 and 28. The bottom side 46 of conductive gel reservoir 28 contacts the patient's skin through the opening 29 in adhesive layer 30. The bottom side 46' of conductive gel reservoir 26 contacts the patient's skin through the plurality of openings 8 in the device 2. The gel in reservoir 26 is preferably a viscous gel that fills the openings 8 such that the gel is in contact with the skin when the blades have penetrated the stratum corneum. The contact between the gel and skin provides a path for the agent to be transported along. If the gel is not in direct contact with the skin initially, typically sweat accumulates in the confined area and provides a path for the transport of agent from the skin.

Device 10 optionally has a feature which allows the patient to self-administer a sampling or monitoring sequence. Upon depression of push button switch 12, the electronic circuitry on circuit board assembly 18 delivers a predetermined DC current to the electrode/reservoirs 22,26 and 24,28 for a sampling interval of predetermined length. The push button switch 12 is conveniently located on the top side of device 10 and is easily actuated through clothing. A double press of the push button switch 12 within a short time period, e.g., three seconds, is preferably used to activate the device for a sampling or monitoring sequence, thereby minimizing the likelihood of inadvertent actuation of the device 10. Preferably, the device transmits to the user a visual and/or audible confirmation of the onset of the sampling interval by means of LED 14 becoming lit and/or an audible sound signal from, e.g., a "beeper". Agent is withdrawn through the patient's skin, e.g., on the arm, by electrotransport over the predetermined sampling interval.

The push button switch 12, the electronic circuitry on circuit board assembly 18 and the battery 32 are adhesively "sealed" between upper housing 16 and lower housing 20. Upper housing 16 is preferably composed of rubber or other elastomeric material, e.g., injection moldable ethylene vinyl acetate. Lower housing 20 is preferably composed of a plastic or elastomeric sheet material (e.g., polyethylene) which can be easily molded to form depressions 25,25' and cut to form openings 23,23'. The assembled device 10 is preferably water resistant (i.e., splash proof) and is most preferably waterproof. The system has a low profile that easily conforms to the body, thereby allowing freedom of movement at, and around, the wearing site. The reservoirs 26 and 28 are located on the skin-contacting side of the device 10 and are sufficiently separated to prevent accidental electrical shorting during normal handling and use.

The device 10 adheres to the patient's body surface (e.g., skin) by means of an adhesive layer 30 (which has upper adhesive side 34 and body-contacting adhesive side 36). The adhesive side 36 covers the entire underneath side of the device 10 except where the device 2 and reservoir 28 are located. The adhesive side 36 has adhesive properties which assures that the device 10 remains in place on the body during normal user activity, and yet permits reasonable removal after the predetermined (e.g., 24-hour) wear period. Upper adhesive side 34 adheres to lower housing 20 and retains the electrodes and gel reservoirs within housing depression 25,25' as well as retains device 2 to lower housing 20 and lower housing 20 to upper housing 16. In one embodiment of the sampling device, there is a release liner (not shown) on the device 10 for maintaining the integrity of the device when it is not in use. In use, the release liner is stripped from the device before the device is applied to the skin.

The preferred form in which an agent is sampled generally determines the type of sampling system to be used. That is, the selection of a "passive" system which samples the agent by diffusion or an electrically powered system which samples the agent by electrotransport will be mostly determined by the form of the agent. For osmotic systems which sample drugs by convective flow carried by a solvent, the agent preferably has sufficient solubility in the carrier solvent. It will be appreciated by those working in the field that the present invention can be used in conjunction with a wide variety of osmotic sampling systems, as the invention is not limited to a particular device in this regard. Osmotic devices are disclosed for example in U.S. Pat. No. 4,756,314 to Eckenhoff et al., U.S. Pat. No. 4,340,480 to Eckenhoff, U.S. Pat. No. 4,655,766 to Theeuwes et al., and U.S. Pat. No. 4,753,651 to Eckenhoff, the disclosures of which are incorporated by reference herein in their entirety. As mentioned above, the member 2 of the present invention can be used with known sampling devices including, but not limited to, reverse iontophoresis, osmosis, passive diffusion, phonophoresis, and suction (i.e., negative pressure).

It will be appreciated by those of ordinary skill in the art that the invention can be embodied in other specific forms without departing from the spirit or essential character thereof. The presently disclosed embodiments are therefore considered in all respects to be illustrative and not restrictive. The scope of the invention is indicated by the appended claims rather than the foregoing description, and all changes which come within the meaning and range of equivalents thereof are intended to be embraced therein.

What is claimed is:

1. A device for piercing the stratum corneum of a body surface to form pathways through which an agent can be withdrawn, comprising:

a sheet having a plurality of microblades formed from the sheet and bent downward therefrom and at least one opening in the sheet adjacent the plurality of microblades; and a collector on the sheet which withdraws the agent through the pathways and collects said agent.

2. The device of claim 1, wherein the collector is positioned to sample the agent from the body surface through an opening in the sheet.

3. The device of claim 1, wherein the collector is a reverse electrotransport device.

4. The device of claim 1, wherein the collector is a passive diffusion device.

5. The device of claim 1, wherein the collector is an osmotic device.

6. The device of claim 1, wherein the collector comprises:

a semi-permeable membrane positioned across an opening in the sheet; and an absorbent pad on the semi-permeable membrane.

7. The device of claim 6, wherein the absorbent pad contains an osmotically active material.

8. The device of claim 1, further comprising an agent sensing element.

9. The device of claim 8, wherein the agent sensing element is a glucose sensor.

10. The device of claim 1, further comprising an activation mechanism such that when activated, the collector performs a collection and monitoring sequence.

11. The device of claim 1, wherein the microblades having a length in the range of about 0.02 mm to about 0.4 mm.

12. A method for transdermally sampling an agent contained in the body of a patient, comprising:

providing a sheet having at least one opening adjacent a plurality of microblades, said microblades formed from the sheet and bent downward therefrom;

forming a plurality of microslits through a stratum corneum of skin of the patient by placing on the skin the sheet to cause said microblades to pierce the stratum corneum; and withdrawing the agent through the microslits and collecting the agent in a reservoir.

13. The method of claim 12, including positioning the collector to sample the agent through an opening in the sheet.

14. The method of claim 12, wherein the agent is withdrawn via reverse electrotransport.

15. The method of claim 12, wherein the agent is withdrawn via passive diffusion.

16. The method of claim 12, wherein the agent is withdrawn via osmosis.

17. The method of claim 12, including withdrawing the agent through a semipermeable membrane.

18. The method of claim 12, including sensing the agent collected in the reservoir.

19. The method of claim 12, wherein the agent is selected from the group consisting of body electrolytes, alcohol, glucose, and drugs.

20. The method of claim 12, wherein the agent is glucose.

21. The method of claim 20, including sensing the glucose collected in the reservoir and signaling the patient in response thereto.

22. The device of claim 12, wherein the microblades having a length in the range of about 0.02 mm to about 0.4 mm.

23. A device for piercing the stratum corneum of a body surface to form pathways through which an agent can be withdrawn, comprising:

a sheet having at least one opening adjacent a plurality of microblades extending from the sheet; and a passive diffusion device on the sheet which collects the agent withdrawn through the pathways.

24. The device of claim 23, wherein the passive diffusion device includes a membrane which draws the agent from the body surface and a reservoir for containing said agent.

25. A device for piercing the stratum corneum of a body surface to form pathways through which an agent can be withdrawn, comprising:

a sheet having at least one opening adjacent a plurality of microblades extending from the sheet; and an osmotic device on the sheet which collects the agent withdrawn through the pathways.

26. The device of claim 25, wherein the osmotic device includes a membrane which draws the agent from the body surface, an absorbent pad containing an osmotically active material, and a reservoir for containing said agent.

27. A device for piercing the stratum corneum of a body surface to form pathways through which an agent can be withdrawn, comprising:

a sheet forming at least one opening adjacent a plurality of microblades extending from the sheet; and a reverse electrotransport device on the sheet which collects the agent withdrawn through the pathways.

28. The device of claim 27, wherein the reverse electrotransport device includes an electrical source connected to a plurality of electrodes and a reservoir for containing the agent, the reservoir being coupled to an electrode.

* * * * *